United States Patent [19]

Seibert

[11] 4,233,223
[45] Nov. 11, 1980

[54] PREPARATION OF 3,3-BIS-(4-DIMETHYLAMINOPHENYL)-6-DIMETHYLAMINOPHTHALIDE

[75] Inventor: Walter Seibert, Ludwigshafen, Fed. Rep. of Germany

[73] Assignee: BASF Aktiengesellschaft, Ludwigshafen, Fed. Rep. of Germany

[21] Appl. No.: 64,759

[22] Filed: Aug. 8, 1979

[30] Foreign Application Priority Data

Aug. 12, 1978 [DE]  Fed. Rep. of Germany ....... 2835450

[51] Int. Cl.² .......................................... C07D 307/88
[52] U.S. Cl. .................................................... 260/343.4
[58] Field of Search ..................................... 260/343.4

[56] References Cited

U.S. PATENT DOCUMENTS

| | | | |
|---|---|---|---|
| 2,742,483 | 4/1956 | Crounse et al. | 260/343.4 |
| 3,185,709 | 5/1965 | Munro et al. | 260/343.4 |
| 3,642,514 | 2/1972 | Orita et al. | 260/343.4 |
| 3,845,077 | 10/1974 | Hughes | 260/343.4 |
| 3,987,062 | 10/1976 | Okada et al. | 260/343.4 |
| 4,052,415 | 10/1977 | Mayer | 260/343.4 |
| 4,076,728 | 2/1978 | Maulding | 260/343.4 |

FOREIGN PATENT DOCUMENTS

| | | | |
|---|---|---|---|
| 1325029 | 8/1973 | United Kingdom | 260/343.4 |
| 1341040 | 12/1973 | United Kingdom | 260/343.4 |
| 1347467 | 2/1974 | United Kingdom | 260/343.4 |
| 1359899 | 7/1974 | United Kingdom | 260/343.4 |

OTHER PUBLICATIONS

Perrine, Jour. of Org. Chem. vol. 16, pp. 1303, 1951.
Aida, Chem. Abst. 84:46059P 1976.

*Primary Examiner*—Henry R. Jiles
*Assistant Examiner*—Jane T. Fan
*Attorney, Agent, or Firm*—Oblon, Fisher, Spivak, McClelland & Maier

[57] ABSTRACT

Crystal violet lactone is prepared by oxidizing 2-(4,4'-bis-dimethylaminobenzhydryl)-5-dimethylaminobenzoic acid in aqueous alkaline solution by means of a water-soluble ferricyanide salt or in the presence of a ferricyanide.

A very pure crystal violet lactone is obtained in high yield.

8 Claims, No Drawings

PREPARATION OF 3,3-BIS-(4-DIMETHYLAMINOPHENYL)-6-DIMETHYLAMINOPHTHALIDE

The present invention relates to a process for the preparation of 3,3-bis-(4-dimethylaminophenyl)-6-dimethylaminophthalide (=crystal violet lactone) by oxidizing 2-(4,4'-bis-dimethylaminobenzhydryl)-5-dimethylaminobenzoic acid.

3,3-Bis-(4-dimethylaminophenyl)-6-dimethylaminophthalide, hereafter referred to as crystal violet lactone or CVL, is of great importance as a dye intermediate for pressure-sensitive copying systems.

The patent literature discloses a plurality of processes for oxidizing 2-(4,4'-bis-dialkylaminobenzhydryl)-5-dialkylaminobenzoic acids, especially 2-(4,4'-bis-dimethylaminobenzhydryl)-5-dimethylaminobenzoic acid, in acid or in alkaline solution (German Laid-Open Applications DOS No. 2,557,687, DOS No. 2,156,662, DOS No. 1,962,881 and DOS No. 2,143,021, U.S. Pat. Nos. 3,987,062, 4,076,728 and 3,185,709, and Japanese Laid-Open Application No. 124,931/1975, reviewed in C.A. 84 (1976) 46,059p).

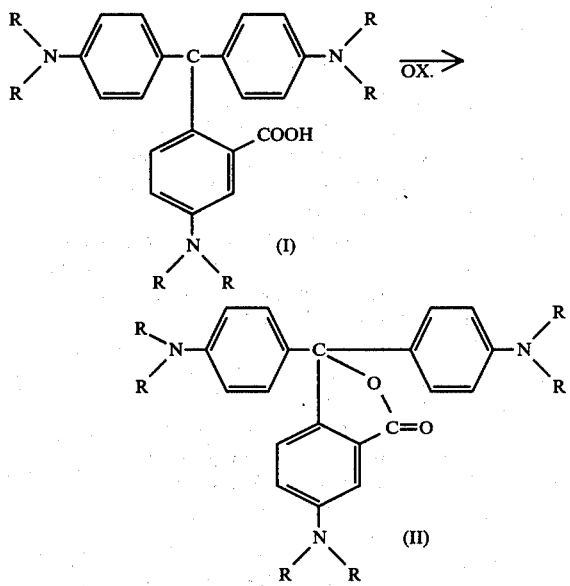

R=alkyl, especially —CH$_3$.

Oxidation in an alkaline solution is suitable especially when the acid, after synthesis or purification, is in the form of a dilute aqueous solution. In many cases, the oxidation is carried out in the presence of an organic solvent in order to improve the particle form of the reaction product and/or to improve the yield (German Laid-Open Application DOS No. 2,156,662; U.S. Pat. No. 3,987,062; and Japanese Laid-Open Application No. 124,931/1975).

The prior art oxidation processes do not give optimum yields of crystal violet lactone. Processes carried out in water in the presence of an organic solvent have the disadvantage that for ecological reasons the solvents present in the mother liquor must be either recovered or be removed in some other way, for example by biological degradation. Both possible methods of removing the solvents entail high costs.

It is an object of the present invention to provide a process for the oxidation of 2-(4,4'-bis-dimethylaminobenzhydryl)-5-dimethylaminobenzoic acid which is carried out in the absence of an organic solvent and gives the corresponding phthalide (II) in high yield and, where possible, in improved purity.

I have found that this object is achieved and that 3,3-bis-(4'-dimethylaminophenyl)-6-dimethylaminophthalide (crystal violet lactone) is obtained in high yield and good purity by oxidizing 2-(4,4'-bis-dimethylaminobenzhydryl)-5-dimethylaminobenzoic acid in aqueous alkaline solution at from 0° to 100° C. and at a pH of from 8 to 12 if the oxidation is carried out with a water-soluble ferricyanide salt or in the presence of a ferricyanide.

Using the process according to the invention, crystal violet lactone is obtained, after recrystallization, in a purity of from 98 to 100% and with a yield of from 88 to 92% of theory. The high yield of crystal violet lactone was surprising, since it is known from J. Org. Chem. 16 (1951), 1,303, that tertiary aliphatic amines containing methyl groups are demethylated by alkaline potassium ferricyanide solutions. Further, the same publication discloses that ferricyanides in alkaline solution are also reduced by dimethylaniline. The yield of CVL obtained by the process according to the invention is substantially higher than in the oxidation process with peroxydisulfates described in German Laid-Open Application DOS No. 2,143,021. From the data in Example 2 of the said DOS, the yield of purified CVL can be calculated to be 72% of theory, but no information on the purity is given.

The process according to the invention is as a rule carried out by dissolving 2-(4,4'-bis-dimethylaminobenzhydryl)-5-dimethylaminobenzoic acid, hereafter also referred to as DABA, in warm water after having added the requisite amount of an alkali metal carbonate or alkali metal hydroxide, and then oxidizing the acid to the lactone with a water-soluble ferricyanide salt.

The weight ratio of water to DABA is in general from 5:1 to 20:1. The amount of alkali metal carbonate and/or alkali metal hydroxide is at least 1.2 equivalents, but advantageously from 4 to 7 equivalents, per mole of DABA. Examples of suitable alkali metal carbonates are potassium carbonate and, preferably, sodium carbonate, and suitable alkali metal hydroxides are especially potassium hydroxide and sodium hydroxide.

The amount of water-soluble ferricyanide salt is at least equal to that required stoichiometrically, and is preferably from 1.0 to 1.2 times the stoichiometric amount, ie. from 2.0 to 2.4 moles of ferricyanide per mole of DABA.

Suitable water-soluble ferricyanide salts are especially the potassium and sodium salt. Instead of commercial potassium ferricyanide, solutions obtained by oxidizing potassium ferrocyanide in the presence of an acid by means of hydrogen peroxide at room temperature may be used.

The oxidation of DABA may be carried out at from 0° to 100° C., advantageously at from room temperature (about 20° C.) to 100° C., preferably at from 30° to 100° C.

The oxidation takes place rapidly and is in general complete in less than 5 hours.

A critical factor determining the reaction rate and the yield is the pH in the reaction mixture, which should not fall below 8. If necessary, the pH is maintained at above 8 by adding further sodium carbonate, potassium carbonate and/or alkali metal hydroxide solution.

After completion of the oxidation, the product is isolated in the conventional manner. The crude lactone is filtered off from the warm or hot solution and is washed neutral with water. It is then purified by recrystallization. Where necessary, basic constituents still present can at the same time be neutralized by adding a small amount of an organic carboxylic acid, eg. acetic acid. This gives a somewhat purer CVL. The recrystallized crystal violet lactone in general has a purity of 98% or more.

The process according to the invention can also be carried out by using a water-soluble ferrocyanide salt in an amount at least equivalent to the stoichiometrically required amount of ferricyanide, and adding at least the stoichiometrically required amount of an oxidizing agent which is capable of oxidizing a ferrocyanide to a ferricyanide.

It is however also possible to use less than the stoichiometrically required amount, and even as little as catalytic amounts, of ferricyanide and/or ferrocyanide and an oxidizing agent which oxidizes a ferrocyanide to a ferricyanide.

For the purposes of the present invention, a catalytic amount means from 2 to 30%, preferably from 5 to 20%, of the stoichiometrically required amount of ferrocyanide and/or ferricyanide. Suitable oxidizing agents which oxidize a ferrocyanide to a ferricyanide are, in particular, hydrogen peroxide and peroxydisulfates, eg. potassium, sodium or ammonium peroxydisulfate. Hydrogen peroxide may be used in commercial concentrations, which are from 3 to 90% by weight. Preferably, solutions of 30% strength by weight or more are used.

The oxidizing agents are used in at least such amount that if less than the stoichiometric amount of ferricyanide is used, the sum of ferricyanide and the other oxidizing agent corresponds at least to the stoichiometrically required amount. Where catalytic amounts of a ferrocyanide and/or ferricyanide are used, at least the stoichiometrically required amount of oxidizing agent is used and, in the case of hydrogen peroxide, preferably from 1 to 4 moles per mole of DABA. In the case of peroxydisulfates, the amount used is preferably from 1.0 to 1.2 times the stoichiometrically required amount (corresponding to from 1 to 1.2 moles per mole of DABA).

In this embodiment of the process according to the invention, the oxidation is advantageously carried out at from 70° to 100° C. At these temperatures, the reaction is as a rule complete in less than 5 hours.

The working up and isolation of the crystal violet lactone, and its purification by recrystallization, are carried out as described above.

The Examples which follow illustrate the process according to the invention. The purity of the 2-(4,4'-bis-dimethylaminobenzhydryl)-5-dimethylaminobenzoic acid used as the starting material was determined by titration with tetrabutylammonium hydroxide (with potentiometric indication). The product used was 99.1% pure. The purity of the crystal violet lactone was determined spectroscopically at 600 nm.

In the Examples which follow, parts and percentages are by weight.

EXAMPLE 1

84.2 parts of 2-(4,4'-bis-dimethylaminobenzhydryl)-5-dimethylaminobenzoic acid of 99.1% purity (=83.4 parts of 100% pure product) are introduced into 1,000 parts of water and, after adding 50 parts of anhydrous sodium carbonate, are dissolved by heating. The resulting pH is 9.6 at 60° C. At this temperature, a solution of 135 parts of potassium ferricyanide in 300 parts of water is run in over 40 minutes, during which the pH drops to about 8.8. The mixture is heated for 5 minutes at 80° C. to obtain the reaction product in a more easily filtrable form. The resulting crystalline crude crystal violet lactone is filtered off and washed with water. For purification, an equal amount by weight of ethylene glycol monobutyl ether (butylglycol) is added to the moist crude lactone (138 parts) and the mixture is heated to 145° C., so that water distils off and the lactone dissolves. The solution is filtered hot to remove small amounts of an inorganic residue, and is then left to crystallize. The crystals are filtered off, washed with a small amount of butylglycol and dried. Yield, 76.4 parts of CVL having a melting point of 179° to 180° C. and a purity of 100%. This corresponds to a yield of 92.0% of theory.

EXAMPLE 2

84.2 parts of 2-(4,4'-bis-dimethylaminobenzhydryl)-5-dimethylaminobenzoic acid (99.1% pure) are introduced into 1,000 parts of water and, after adding 70 parts of anhydrous sodium carbonate, are dissolved at 60° C. The solution is allowed to cool to 30° C., whilst stirring, whereupon the greater part of the acid precipitates out as fine crystals of the sodium salt (pH of the suspension 10.3). After adding 30 parts of potassium ferrocyanide, a solution of 53 parts of sodium persulfate in 150 parts of water is run in over 25 minutes, during which the temperature rises to 42° C. and the pH drops to 9.6. The mixture is heated to 80° C. to obtain a product which is easily filtrable, and the latter is then isolated and purified as described in Example 1. Yield, 74.2 parts of CVL having a melting point of 178°–179.5° C. and a purity of 98.9%. This corresponds to a yield of 88.4% of theory.

EXAMPLE 3

84.2 parts of 2-(4,4'-bis-dimethylaminobenzhydryl)-5-dimethylaminobenzoic acid (99.1% pure) are introduced into 1,000 parts of water and, after adding 70 parts of anhydrous sodium carbonate, are dissolved at 60° C. The solution is allowed to cool to 30° C., whilst stirring, whereupon the greater part of the acid precipitates out as fine crystals of the sodium salt (pH of the suspension 10.0). A mixture of 173 parts of potassium ferrocyanide, 200 parts of 10% strength sulfuric acid and 125 parts of 6% strength hydrogen peroxide, which has been prepared at room temperature about 6 hours previously, is then run in over 3 minutes. The pH drops to about 9.5, and the temperatures rise slightly. The mixture is heated to 80° C. to give an easily filtrable product.

The latter is then isolated and purified as described in Example 1. Yield, 77.0 parts of CVL having a melting point of 178°–180° C. and a purity of 98.5%. This corresponds to a yield of 91.4% of theory.

EXAMPLE 4

84.2 parts of 2-(4,4'-bis-dimethylaminobenzhydryl)-5-dimethylaminobenzoic acid (99.1% pure) are introduced into 1,000 parts of water and, after adding 70 parts of anhydrous sodium carbonate, are dissolved at elevated temperature. After adding 43.25 parts of potassium ferrocyanide, the mixture is heated to 95° C., and 40.8 parts of 50% strength hydrogen peroxide are added dropwise over 4 hours. Stirring is then continued for 20 minutes after which the coarse crystals of lactone are filtered off hot.

The latter are then purified as described in Example 1. Yield, 75.3 parts of CVL having a melting point of 176°–178° C. and a purity of 98.5%. This corresponds to a yield of 89.6% of theory.

EXAMPLE 5

84.2 parts of 2-(4,4'-bis-dimethylaminobenzhydryl)-5-dimethylaminobenzoic acid (99.1% pure) are dissolved in 1,000 parts of water after having added 0.2 mole of sodium hydroxide. The pH in the solution is brought to 10–10.5 by adding sodium hydroxide solution. The oxidation is carried out as described in Example 4, except that the pH in the reaction mixture is kept at from 9.5 to 10 by adding sodium hydroxide solution.

The product is worked up, and recrystallized, as described in Example 4. The yield and purity of the product correspond to that of the product obtained according to Example 4.

I claim:

1. In a process for the preparation of 3,3-bis-(4-dimethylaminophenyl)-6-dimethylaminophthalide (crystal violet lactone) by oxidizing 2-(4,4'-bis-dimethylaminobenzhydryl)-5-dimethylaminobenzoic acid in aqueous alkaline solution at from 0° to 100° C. and at a pH of from 8 to 12, the improvement that the oxidation is carried out with a water-soluble ferricyanide salt or in the presence of a ferricyanide.

2. A process as claimed in claim 1, wherein not less than the stoichiometrically required amount of a water-soluble ferricyanide salt is employed.

3. A process as claimed in claim 1, wherein from 2 to 2.4 moles of ferricyanide are employed per mole of benzoic acid derivative.

4. A process as claimed in claim 1, wherein an amount which is less than that stoichiometrically required, and may be merely a catalytic amount, of a ferrocyanide, a ferricyanide or a mixture thereof is used, together with an oxidizing agent which oxidizes a ferrocyanide to a ferricyanide.

5. A process as claimed in claim 1, wherein from 2 to 30% of the stoichiometrically required amount of a ferricyanide, a ferrocyanide or a mixture thereof is used, together with an oxidizing agent which oxidizes a ferrocyanide to a ferricyanide.

6. A process as claimed in claim 4, wherein an alkali metal peroxydisulfate, ammonium peroxydisulfate, hydrogen peroxide or a mixture of these is used as the oxidizing agent.

7. A process as claimed in claim 5, wherein an alkali metal peroxydisulfate, ammonium peroxydisulfate, hydrogen peroxide or a mixture of these is used as the oxidizing agent.

8. A process as claimed in claim 4 or 5, wherein from 1 to 4 moles of hydrogen peroxide or from 1 to 1.2 moles of peroxydisulfate are used per mole of 2-(4,4'-bis-dimethylaminobenzhydryl)-5-dimethylaminobenzoic acid.

* * * * *